United States Patent
Szafranski et al.

(10) Patent No.: US 8,303,872 B2
(45) Date of Patent: Nov. 6, 2012

(54) ETHYLENE UREA DISPLAYING LASTING POWDER FLOW

(75) Inventors: Henry Szafranski, Mannheim (DE);
Stefanie Werland, Mannheim (DE);
Peter Raatz, Ludwigshafen (DE);
Joachim Simon, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 218 days.

(21) Appl. No.: 12/747,313

(22) PCT Filed: Dec. 10, 2008

(86) PCT No.: PCT/EP2008/067193
§ 371 (c)(1),
(2), (4) Date: Jun. 10, 2010

(87) PCT Pub. No.: WO2009/080513
PCT Pub. Date: Jul. 2, 2009

(65) Prior Publication Data
US 2010/0261015 A1   Oct. 14, 2010

(30) Foreign Application Priority Data

Dec. 21, 2007 (EP) .................................. 07150393

(51) Int. Cl.
*B29B 9/00* (2006.01)
*C07D 233/34* (2006.01)

(52) U.S. Cl. ................. 264/144; 264/140; 548/326.1

(58) Field of Classification Search .................. None
See application file for complete search history.

(56) References Cited

U.S. PATENT DOCUMENTS

| 1,775,177 | A | * | 9/1930 | Taylor ............................ 264/144 |
| 2,436,311 | A | | 2/1948 | Larson et al. |
| 2,497,309 | A | | 2/1950 | Larson et al. |
| 2,504,431 | A | | 4/1950 | Loder |
| 2,526,757 | A | | 10/1950 | Larson et al. |
| 2,751,394 | A | | 6/1956 | Marotta et al. |
| 2,847,698 | A | * | 8/1958 | Ritterson ...................... 425/223 |
| 2,993,906 | A | | 7/1961 | Sprenger et al. |
| 4,795,604 | A | * | 1/1989 | Matsuzaki et al. ............. 264/144 |
| 5,340,509 | A | * | 8/1994 | Chang et al. ...................... 264/5 |
| 2007/0131381 | A1 | | 6/2007 | Schermutzki et al. |

FOREIGN PATENT DOCUMENTS

DE  10 2005 054 462   5/2007

OTHER PUBLICATIONS

U.S. Appl. No. 13/255,805, filed Sep. 9, 2011, Wigbers, et al.
Van't Land, C.M. "Industrial Crystallization of Melts", Marcel Dekker, New York, (chapter 3 and 4), pp. 45-116) (2005).

* cited by examiner

*Primary Examiner* — Mary F Theisen
(74) *Attorney, Agent, or Firm* — Oblon, Spivak, McClelland, Maier & Neustadt, L.L.P.

(57) ABSTRACT

The present invention relates to a process for preparing ethylene urea in solid form, in which a water-comprising product melt of ethylene urea is cooled on a breaking-up apparatus and the water content of the solid obtained is from 5 to 15% by weight. Furthermore, the invention relates to ethylene urea as solid prepared by a process according to the invention, wherein the water content of the solid is from 5 to 15% by weight and the solid displays lasting powder flow.

6 Claims, No Drawings

ETHYLENE UREA DISPLAYING LASTING POWDER FLOW

The present invention relates to a process for preparing ethylene urea in solid form, in which a water-comprising product melt of ethylene urea is cooled on a breaking-up apparatus and the water content of the solid obtained is from 5 to 15% by weight. Furthermore, the invention relates to ethylene urea as solid prepared by a process according to the invention, wherein the water content of the solid is from 5 to 15% by weight and the solid displays lasting powder flow.

Ethylene urea (2-imidazolidone, imidazolidin-2-one) is used in a wide variety of ways in process technology. It is of importance as an intermediate for, inter alia, the pharmaceuticals industry. Ethylene urea is also used in the production of plasticizers, surface coatings, polymers and also textile and leather auxiliaries. Processing is, depending on the field of use, carried out continuously or batchwise, for example in stirred reactors.

The preparation of ethylene urea from various starting materials has been known for a long time. The patents U.S. Pat. Nos. 2,436,311, 2,504,431 and 2,526,757 propose the preparation of ethylene urea from ethylenediamine and urea in the presence of water. The ethylene urea obtained is separated off from the crude product, freed of water and residual ethylenediamine and subsequently conveyed over a flaking roller. Production and packaging of the flakes has to occur with exclusion of air. As an alternative, the product can be crystallized from a suitable solvent.

U.S. Pat. No. 2,497,309 describes a process which corresponds to that mentioned above with the exception that carbon dioxide is used as starting material instead of urea.

U.S. Pat. No. 2,751,394 proposes the addition of stabilizers, for example citric acid, to the ethylene urea to improve the color stability of the finished product. The ethylene urea can have been prepared from ethylenediamine and urea. The end product can be in the form of either an aqueous solution or a solid, e.g. as flakes. In this process, too, essentially all water is removed from the ethylene urea melt.

U.S. Pat. No. 2,993,906 discloses the purification of imidazolidones, especially ethylene urea, with the aim of obtaining a white, odorless and crystalline solid. This is achieved by bringing an aqueous solution of ethylene urea into contact with an ion exchange resin. A clear melt is obtained from the aqueous solution and this is cooled to give a crystalline mass. This mass is milled to a fine powder and dried. The product comprises unspecified amounts of the ion exchange resin used for purification.

The application DE 10 2005 054 462 A1 describes a process for palletizing urea and a palletizing plant suitable for this purpose. Application of a thin product solvent film enables a constant pellet quality to be ensured for hygroscopic products even at high atmospheric humidity. The products are essentially dry and take up only a very small amount of liquid during processing.

It was an object of the process of the invention to indicate an inexpensive way of preparing a nondusting ethylene urea which displays lasting powder flow. In particular, the product should be able to be emptied out of a closed container, for example a sack or a drum, by simple tipping even after storage for a number of months in the container without mechanical aids having to the used for loosening. A further object of the present invention was to provide a white to pale yellow product. In particular, the product should not discolor or not discolor significantly during storage.

This object is achieved by the aspects of the invention. One aspect of the invention is a process for preparing ethylene urea in solid form, in which a product melt of ethylene urea having a water content of from 5 to 15% by weight is cooled by means of a breaking-up apparatus and the solid obtained has essentially the same water content as the product melt.

The invention further provides ethylene urea in solid form which can be obtained by a process according to the invention, wherein the water content of the solid is from 5 to 15% by weight.

Ethylene urea prepared by a process according to the invention can be used in a variety of ways, for example in chemical syntheses as reactant or as component of a mixture. Ethylene urea is used, inter alia, for producing plasticizers, surface coatings and pharmaceuticals. The invention further provides for the use of the ethylene urea according to the invention or the ethylene urea prepared by a process according to the invention for producing surface coatings and also textile and leather auxiliaries. In the production of surface coatings and also in the textile and leather industry, ethylene urea is used, in particular, as formaldehyde scavenger.

Preferred embodiments may be found in the claims and the description. Combinations of preferred embodiments are also comprised by the invention.

Ethylene urea can be prepared industrially by reaction of 1,2-ethylenediamine with urea, in which these two starting materials are mixed and heated to a temperature of at least 260° C. This forms a crude melt which comprises the desired compound and ammonia and also water-insoluble by-products. The crude melt is usually quenched rapidly to temperatures of about 150° C. by means of a suitable solvent, preferably water. This gives an aqueous solution having an ethylene urea content of, for example, about 80%. The aqueous solution is generally freed of the water-insoluble secondary components, for example by filtration. The desired product ethylene urea is generally isolated from the aqueous solution by crystallization in a further process step. The crystals can be separated from the solution by known methods, for example by centrifugation in a screen screw centrifuge. The crystallized ethylene urea produced in this way still comprises from about 5 to 15% by weight, e.g. from 8 to 12% by weight, usually about 10% by weight, of water.

If this product is stored, the moist crystals adjoin onto one another and the mass clumps together to form a solid block within a few hours. This property of commercial ethylene urea means that the product cannot, for example, readily be metered into a container by the user but has to be broken up mechanically before further use.

One way of preventing clumping together is to dry the moist crystals in a suitable drying apparatus, for example a paddle dryer. This step is comparatively complicated and gives a finely pulverulent, dusting product which can be stirred into a batch only with difficulty since it floats on the surface.

It has surprisingly been found that clumping together can be avoided by means of an alternative process which is described in more detail below.

According to the invention, a water-comprising product melt of ethylene urea is cooled by means of a breaking-up apparatus and converted into a solid. The water-comprising product melt can be produced in various ways. In an advantageous embodiment, the crystallized ethylene urea is melted at temperatures of from 50 to 120° C., preferably from 80 to 100° C. This gives, as a function of the amount of water enclosed in the crystals, a product melt comprising from 85 to 95% by weight, e.g. from 88 to 92% by weight, usually about 90% by weight, of ethylene urea. To ensure a water content of the product melt in the range according to the invention, it is possible to provide further process steps, for example a distillation. However, such additional process steps are generally not necessary.

In a further advantageous variant, the crude melt obtained from the reaction is quenched with water, for example by introducing the crude melt into a reservoir of water or introducing water into the melt. The melt is in this way generally brought to a temperature of from 50 to 120° C., preferably from 80 to 100° C. Water-insoluble by-products can be separated off from the melt, for example by conventional methods such as filtration.

The product melt produced by one of the two variants described has a water content of from 2 to 18% by weight, preferably from 5 to 15% by weight, particularly preferably from 8 to 12% by weight.

It is in principle possible to use any breaking-up apparatus which can be cooled for the process of the invention. In a preferred embodiment, the breaking-up apparatus comprises essentially a flaking roller. A flaking roller is usually a hollow metal cylinder which is cooled internally by means of a cooling medium, preferably water. The temperature on the outside of the roller is preferably from 10 to 30° C. The product melt can be brought into contact with the roller in various ways. The melt is frequently placed in a heatable pan. The roller dips partly into the pan and continuously takes up product as it rotates. The product can also be applied to the flaking roller by means of a separate, typically smaller, take-up roller. An alternative to dipping into a pan is feeding the melt from the side or from above onto the flaking roller. A system of two contrarotating flaking rollers in which the melt is, for example, fed in at the point at which the two rollers have the smallest distance between them is also possible. The product melt is cooled on the roller and solidifies. The solidified material is taken off from the flaking roller by means of an offtake device, for example a stripper or knife. This usually gives flakes having an irregular shape. It is also possible to obtain films, granules, needles or other geometric shapes by appropriate choice of the offtake device. Operating parameters such as film thickness or rotational speed of the roller can be determined by a person skilled in the art by means of known methods.

Flaking belts represent an alternative form of the breaking-up apparatus according to the invention. They usually consist of a thin belt running in a loop, for example a stainless steel strip having a thickness of about 1 mm. The upper part of the belt is generally sprayed from below with a cooling medium, usually water, so that the surface of the belt preferably has a temperature of from 10 to 30° C. The product melt can be applied to the belt in various ways. One possibility is a system comprising two contrarotating rollers in the middle of which the melt is introduced. The thickness of melt applied to the belt can be adjusted via the spacing of the rollers, their rotational speed and the speed of the belt. As an alternative, the melt can be applied uniformly to the belt by means of a pan having an overflow. The melt solidifies on the belt and is typically removed from the belt at the point at which the belt changes direction by means of an offtake device. The offtake device can be a stripper, scraper or another device which is suitable for detaching the solidified material from the belt. The offtake device can also be configured so that it breaks up the solidified material. An example is a roller system which breaks the plates detached from the belt into flakes.

A further embodiment of the breaking-up apparatus according to the invention is a palletizing belt having a similar construction to that described in DE 10 2005 054 462 A1. Its function is comparable to that of an above-described flaking belt. However, the product melt is not applied in the form of a film to the belt but as individual drops which solidify to form pellets due to cooling of the belt. The shaping of the drops is frequently achieved by means of a rotor-stator system in which a perforated outer cylinder rotates around an inner stator. The product melt is applied from the inside via the stator to the perforated cylinder. The melt runs through the holes onto the belt and is sheared into individual drops due to the rotation of the outer cylinder.

A comprehensive overview of palletizing belts, flaking belts and flaking rollers and also their design may be found in the book by C. M. Van't Land: Industrial crystallization of melts, Marcel Dekker, New York, 2005 (chapters 3 and 4, pp. 45-116).

The flakes or pellets formed have essentially the same water content as the product melt. Shape and size of the flakes depend on the breaking-up apparatus used. The flakes typically have an irregular shape. Their length and width are generally each from 0.5 to 3 cm, preferably from 1 to 2 cm. The thickness of the flakes is generally from 0.1 to 3 mm, preferably from 0.2 to 2 mm. The pellets preferably have an essentially circular cross section of from 5 to 10 mm, are flat on the bottom and convex at the top.

The pH of the ethylene urea flakes or pellets dissolved in water is typically in the range from 10 to 11, preferably 10.5, measured in a 10 percent strength ethylene urea solution at 20° C. The flakes have a dry feel.

If the product melt is obtained from crystallized material, the flakes or pellets are white having a color number of less than 80 APHA, preferably less than 50 APHA, particularly preferably less than 20 APHA. The flakes or pellets give a clear solution when they are stirred into water. Neither the flakes or pellets themselves nor the aqueous solution have an appreciable odor.

If the product melt is produced directly from the crude melt, as described in an alternative variant, the flakes or pellets are white to light yellowish and have a color number of less than 250 APHA, preferably less than 200 APHA, particularly preferably less than 150 APHA. When stirred into water, slight turbidity is obtained. The flakes or pellets and their aqueous solution can smell slightly of ammonia.

In contrast to the crystallized material, the ethylene urea in solid form prepared by the process of the invention, in particular the flakes or pellets, does not cake and still displays powder flow even after storage for a number of months in fixed containers such as sacks or drums. This is all the more surprising since the flakes or pellets have essentially the same water content as the crystallized material.

The following examples illustrate the process of the invention without restricting the invention to these variants.

EXAMPLE 1

2500 kg of crystallized ethylene urea are introduced into a heatable stirred vessel, heated to 80° C. and thus melted in its own water of crystallization. This product melt was conveyed in amounts of from 100 to 300 kg/h directly onto a flaking roller cooled to 25-33° C. by means of water. This gave 2440 kg of white, about 0.5-1 mm thick, irregularly shaped flakes of ethylene urea. Length and width were each from about 1 to 2 cm. The flakes had a dry feel but had the same water content as the crystallized material since no process step in which the water could have been separated off was present between melting and flaking.

EXAMPLE 2

4000 kg of a hot melt of crude ethylene urea obtained from the reaction of ethylenediamine with urea was admixed as quickly as possible with 400 kg of water in a stirred vessel and cooled down to 80° C. The product melt obtained in this way was firstly filtered a number of times at 80° C. through a centrifugal disk filter and subsequently conveyed at a flow rate of from 100 to 300 kg/h onto a flaking roller cooled to 25-33° C. by means of water. This gave 4200 kg of white to pale yellow, about 0.5-1 mm thick, irregularly shaped flakes of ethylene urea. Length and width were each from about 1 to 2 cm. Despite a water content of about 9% by weight, the flakes had a dry feel.

In both examples, a steel flaking roller having a width of 2000 mm and a diameter of 1000 mm was used. The rotational speed during flaking was from 1 to 2 rpm, with the ethylene urea melt firstly being applied slowly and then increasingly quickly to the flaking roller. The ethylene urea film on the flaking roller had a thickness of about 1 mm.

The quantity difference between starting materials and product obtained of 60 and 200 kg, respectively, in the above examples was due to an empty, clean flaking roller being used in each case and residual amounts remaining in the apparatus after the end of the experiments. In continuous operation of the flaking roller, these residual amounts would not alter significantly.

The drums (70 kg—PE drums) were stored and opened after storage for one week, three months, six months and one year. The drums could be emptied without problems by inverting even after storage for one year. Even the flakes located at the bottom of the drum had not been appreciably compacted by the pressure of the material on top. No change in the color number and the water content of the flakes was observed during storage in the tightly closed drums.

The invention claimed is:

1. A process for preparing ethylene urea in solid form, comprising cooling a product melt of ethylene urea having a water content of from 5 to 15% by weight by a breaking-up apparatus, wherein a solid obtained has essentially the same water content as the product melt.

2. The process according to claim 1, wherein the product melt and the solid have a water content of from 8 to 12% by weight.

3. The process according to claim 1, wherein the water-comprising product melt is obtained by a process comprising melting crystallized ethylene urea.

4. The process according to claim 1, wherein the water-comprising product melt is obtained by a process comprising admixing a crude melt of ethylene urea with water.

5. The process according to claim 1, wherein the breaking-up apparatus is a flaking roller or a flaking belt.

6. The process according to claim 1, wherein the breaking-up apparatus is a palletizing belt.

* * * * *